US012649654B2

(12) United States Patent
Joó et al.

(10) Patent No.: US 12,649,654 B2
(45) Date of Patent: Jun. 9, 2026

(54) HYDROGEN STORAGE BASED ON AQUEOUS FORMATE- BICARBONATE (HYDROGEN CARBONATE) EQUILIBRIUM

(71) Applicant: GEOMAX PROJECT KFT., Budaörs (HU)

(72) Inventors: Ferenc Joó, Debrecen (HU); Gábor Csaba Papp, Debrecen (HU); János Elek, Debrecen (HU); Henrietta Horváth, Debrecen (HU)

(73) Assignee: Hydrogen Revolution Hungary Kft., Budaörs (HU)

( * ) Notice: Subject to any disclaimer, the term of this patent is extended or adjusted under 35 U.S.C. 154(b) by 215 days.

(21) Appl. No.: 18/575,842

(22) PCT Filed: Jul. 1, 2022

(86) PCT No.: PCT/HU2022/050056
§ 371 (c)(1),
(2) Date: Dec. 30, 2023

(87) PCT Pub. No.: WO2023/275578
PCT Pub. Date: Jan. 5, 2023

(65) Prior Publication Data
US 2024/0327207 A1      Oct. 3, 2024

(30) Foreign Application Priority Data

Jul. 2, 2021      (HU) ..................................... 2100254
Apr. 13, 2022      (HU) ..................................... 2200115

(51) Int. Cl.
| | |
|---|---|
| *C01B 3/0015* | (2026.01) |
| *B01J 23/46* | (2006.01) |
| *C07C 51/41* | (2006.01) |

(52) U.S. Cl.
CPC ........... *C01B 3/0015* (2013.01); *B01J 23/468* (2013.01); *C07C 51/41* (2013.01); *B01J 2231/62* (2013.01);
(Continued)

(58) Field of Classification Search
CPC ..... H01M 8/06; B01J 23/468; B01J 2531/827
See application file for complete search history.

(56) References Cited

U.S. PATENT DOCUMENTS

| | | |
|---|---|---|
| 2016/0303554 A1 | 10/2016 | Gyorvárinéhorváth et al. |
| 2018/0123153 A1 | 5/2018 | Sasson et al. |

FOREIGN PATENT DOCUMENTS

| | | |
|---|---|---|
| CN | 105916803 A | 8/2016 |
| DE | 102006030449 A1 | 1/2007 |
| WO | 2015040440 A2 | 3/2015 |

OTHER PUBLICATIONS

Hull et al., Nature chemistry, 2012, 4(5), 383-388.
(Continued)

*Primary Examiner* — Khanh T Nguyen
(74) *Attorney, Agent, or Firm* — Daniel S. Kim

(57) ABSTRACT

The subject of the invention is a process for the hydrogenation of hydrogen carbonate in an aqueous reaction system, where the process ensures that the hydrogen carbonate, hydrogen and catalyst come into contact with each other while carbon dioxide is present in the gas space. In this phase of the process, formate is produced. The subject of the invention is also a process for the catalytic decomposition of formate in an aqueous reaction system and the hydrogenation of hydrogen carbonate produced in the same reaction system according to the invention, where the reactants and the reaction products are formed in a reversible reaction cycle using the reaction system according to the invention, and this reaction cycle is repeated in the required number of times. In the mentioned formate mg decomposition process,
(Continued)

the formate and the catalyst come into contact, so that hydrogen gas and hydrogen carbonate free of COX by-products are produced as the product of the reaction. Further subject of the invention is a hydrogen storage system based on the method according to the invention, preferably a hydrogen accumulator. Further subject of the invention is a hydrogen storage system according to the invention, preferably the use of a hydrogen accumulator for the storage of hydrogen required for the operation of a fuel cell (or other equipment requiring H2) and, where appropriate, for its release in as needed.

18 Claims, 4 Drawing Sheets

(52) U.S. Cl.
CPC ...... *B01J 2231/76* (2013.01); *B01J 2523/827* (2013.01)

(56) References Cited

OTHER PUBLICATIONS

Joó et al., Chemical Communications 1999, 971-972.
Elek et al., Applied Catalysis A: General 2003, 255, 59-67.
Laurenczy et al., Inorg. Chem.2000, 39, 5083-5088.
Horváth et al., ChemSusChem, (2015) vol. 8(18), 3036-3038.
Udvardy et al., Coordination Chemistry Reviews 438 (2021).

HYDROGEN STORAGE BASED ON AQUEOUS FORMATE- BICARBONATE (HYDROGEN CARBONATE) EQUILIBRIUM

This is the national stage of International Application PCT/HU2022/050056, filed Jul. 1, 2022.

The subject of the invention is a process for the hydrogenation of hydrogen carbonate in an aqueous reaction system, where the process comprises contacting the hydrogen carbonate, hydrogen and catalyst with each other while carbon dioxide is present in the gas space. In this phase of the process, formate is produced. The subject of the invention is also a process for the catalytic decomposition of formate in an aqueous reaction system and the hydrogenation of hydrogen carbonate produced in the same reaction system according to the invention, where the reactants and reaction products are formed in a reversible reaction cycle using the reaction system according to the invention, and this reaction cycle is repeated in the required number of times.

In the mentioned formate decomposition process, the formate and the catalyst come into contact, so that hydrogen gas and hydrogen carbonate free of COx by-products are produced as the product of the reaction. The subject of the invention is also the hydrogen storage system based on the process according to the invention, preferably a hydrogen accumulator. The subject of the invention is also the use of the hydrogen storage system according to the invention, preferably hydrogen accumulator for the storage of hydrogen required for the operation of a fuel cell (or other device requiring $H_2$) and, optionally, for its release as needed.

THE STATE OF THE ART

Hull et al. in their publication (Nature chemistry, 2012, 4(5), 383-388) [1] disclose a reversible hydrogen storage system using $CO_2$ and an iridium catalyst, which operates under near-ambient conditions. In the demonstrated system, $CO_2$ is converted to formate/formic acid at alkaline pH. Although the authors state that dissolved $CO_2$ was essential for the production of formate, and a very small amount of the product was formed when only bicarbonate was used, they even suggest that the catalyst tested there reduces $CO_2$ and not bicarbonate; at the same time, they do not provide the numerical data supporting these findings or the experiments carried out. Table 1 in the referenced publication does not indicate the experimental conditions under which the results cited from the literature were obtained, although the text of the referenced publication indicates that the conditions (pressure, temperature) used in the cited publications are stronger than those used in the referenced publication used by the authors of the article (Hull et al.).

Joó et al. in their publication (Chemical Communications 1999, 971-972) [2], disclosed the homogeneous hydrogenation of aqueous hydrogen carbonate to formate with different catalysts and investigated the effect of the carbon dioxide present. On one hand, they found that for the [RhCl (mtppms)₃] catalyst, $CO_2$ in the gas phase was essential for high reaction rates (although a much slower reaction still occurred in its absence). On the other hand, it was also found that $CO_2$ decreased the rate of reactions carried out with [RuCl₂(mtppms)₂]₂ and [RuCl₂(pta)₄] catalysts. As a consequence, the effect of $CO_2$ on the rate of hydrogenation of bicarbonate cannot be predicted in advance even in the case of catalysts with apparently very similar composition and structure, such as the two catalysts mentioned above, thus the rate-increasing or decreasing effect can only be determined based on experiments. In other words, it is not obvious to one skilled in the art that, for a given catalyst, $CO_2$ present in the gas space will increase or decrease the rate of hydrogenation of bicarbonate.

In their publication Elek et al. (Applied Catalysis A: General 2003, 255, 59-67) [3], disclose that the rate of $NaHCO_3$ hydrogenation catalyzed by the [RuCl₂(mtppms)₂]2 complex at constant $NaHCO_3$ concentration and (at also constant) 6 bar $H_2$ pressure using 5 bar $CO_2$ was 10% lower than in the absence of $CO_2$.

In general, it can be stated that it is difficult to compare the large number of results collected in the literature, that the experimental conditions used were significantly different. This does not only mean the difference in pressure, temperature, and reaction time, but also the difference in the concentration and concentration ratios of the substances used in the reactions. Thus, e.g. starting from the fact that theoretically both $HCO_3^-$ and $CO_2$ can be hydrogenated, during the experiments described in several publications, for example in the publication of Laurenczy et al. (Inorg. Chem. 2000, 39, 5083-5088) [4], the combined dissolved $CO_2$ and $HCO_3^-$ concentration (i.e. the total concentration of carbonaceous inorganic particles in solution) was kept constant during certain experiments. This e.g. had the consequence that in order to examine the $CO_2$ effect, when increasing the $CO_2$ pressure, the amount of measured $NaHCO_3$ had to be reduced, which resulted in a much faster decrease in pH (and thus a faster increase in the formate concentration) than if the carbon dioxide gas pressure had been increased at a constant $HCO_3^-$ concentration. There is also an example of the latter experimental arrangement (in fact, it is the more general one).

The authors of the above-mentioned publications ([2]-[4]) clearly state that the real substrate of bicarbonate hydrogenation is the $HCO_3^-$ anion, even in the presence of $CO_2$. In this context, it is necessary to define what is considered a substrate in a chemical transformation. In our opinion, a substrate is the type of starting material on which the chemical transformation takes place, and which appears in a changed form in the product of the reaction. Determining this is not always easy if various exchange processes take place during the reaction. (Substrate and reactant are not 100% synonymous with each other, because a reactant can also be an auxiliary substance, e.g. a proton-binding base, etc.). During the hydrogenation of bicarbonate in the presence of $CO_2$, $CO_2$ can (also) be a substrate if it is itself directly hydrogenated to formate. However, if its role is limited only to pH adjustment (forming an acidic environment), then it is considered a simple auxiliary material. From the point of view of the present invention, the measurement results that have been published so far in the literature are not sufficient to decide the question.

The following considerations are based on the work of J. N. Butler "Carbon Dioxide Equilibria and Their Applications" (Lewis Publishers, Chelsea, USA, 1991) [5] and X. Li et al. (Fluid Phase Equilibria 2018, 458, 253-263) [6] and use the data available there. The reference to approximations refers to the fact that the activity coefficients were considered to be 1 in the calculations, and e.g. the effect of ionic strength was not taken into account.

Henry's law applies to the dissolution of carbon dioxide in water: [$[CO_2]=K_H \times P(CO_2)$, i.e. increasing the pressure of carbon dioxide linearly increases the concentration of dissolved (hydrated) $CO_2$. If the concentration of dissolved carbon dioxide is given in mol/liter (M) units, and the pressure of gaseous carbon dioxide is given in atm (with a good approximation in bar units), then the value of Henry's constant for pure water at 25° C. is $K_H=10^{-1.5}=0.0316$; and at 35° C., $K_H=10^{-1.7}=0.0200$. This value decreases with increasing temperature and also changes with ionic strength, but this does not significantly affect the following considerations. As the $CO_2$ pressure increases, the dissolved $CO_2$ concentration also increases, and at 25° C. it is approximately 0.0316 M (1 bar), 0.316 M (10 bar), and 3.16 M (100 bar). The acid dissociation constant of the dissociation equilibrium $H_2CO_3=HCO_3^-+H^+$ is $pK_{a1}=6.35$ (25° C.) and 6.309 (35° C.), respectively. For a given pH, the relationship between bicarbonate anion concentration and $CO_2$ pressure can be given by the following formula:

$$\log [HCO_3^-] = pK_{a1} + pK_H + \log P(CO_2) + pH$$

Accordingly, and as can be read from the formula, the equilibrium bicarbonate concentrations also increase due to the larger amounts of $CO_2$ dissolved under higher pressure. According to the measurement data published in Butler's mentioned publication [5], in $NaHCO_3$ solutions with a solvent concentration of m=1 mol/kg, at 35° C., under different $P(CO_2)$ pressures, the equilibrium pHs shown in the table below are formed (column 2), from which the equilibrium $HCO_3^-$ concentrations in column 3 can be calculated.

| Reference table 1 | | |
|---|---|---|
| $P(CO_2)$ (bar) | pH | $[HCO_3^-]$ (M) |
| 9.2 | 6.99 | 1.13 |
| 20.0 | 6.86 | 1.83 |
| 92.8 | 6.33 | 2.50 |

As the solution placed under $CO_2$ pressure initially contained $NaHCO_3$ at a concentration of 1 M (at this temperature and concentration, the concentration of the $NaHCO_3$ solution expressed in molality and molarity is practically the same), the increase in $[HCO_3^-]$ concentration under the influence of 9.2 bar $CO_2$ is only 13% and even at 20 bar CO2 is only 83%. It can also be seen that the concentration of the bicarbonate ion changes non-linearly with the increase in $CO_2$ pressure, the more than 10-fold increase of which (from 9.2 bar to 92.8 bar) entails only a little more than a two-fold increase in the bicarbonate concentration. The reason for this phenomenon is that $H_2CO_3$ and $HCO_3^-$ formed from dissolved carbon dioxide form a buffer solution. From these considerations, it follows that if the catalytic hydrogenation is first order with respect to the substrate, then the initial rate of hydrogenation should vary linearly with the pressure of $CO_2$ if dissolved $CO_2$ itself were the substrate. If, on the other hand, the substrate of the hydrogenation is the bicarbonate anion, then increasing the CO2 pressure is followed by an increase in the reaction rate to a lesser extent. Some of the experiments really showed this, but there are also different experiences. Such e.g. the already mentioned decrease in the rate of hydrogenation when the $CO_2$ pressure is increased ([2] and [3]).

It is interesting that although the equilibrium (i.e. actually existing in the reaction mixture) $HCO_3^-$ concentration can be much higher under $CO_2$ pressure than in the absence of $CO_2$, according to the data published in the literature, this is rarely reflected in the experimentally achieved final formate concentrations, which usually do not exceed the measured $HCO_3^-$ concentration. In some cases, however, in the presence of $CO_2$, the formation of more formate (specifically formic acid, $HCO_2H$) than the amount of bicarbonate ($HCO_3^-$) taken in was detected, the amount of which rarely exceeded 30-40% of the taken bicarbonate. The formation of $HCO_2H$ can only be interpreted as the hydrogenation of dissolved (hydrated) $CO_2$ in addition to or instead of bicarbonate. The logical question arises as to whether the higher formate concentration found in the acidic medium during the given time, compared to the yields achieved with pure $H_2$, comes from the higher hydrogenation of the $CO_2$ added to the gas space or the $HCO_3^-$ already present in the solution. In other words: which substrate does the reaction mechanism prefer, i.e. how much proportion of the product comes from bicarbonate, or how much of the dissolved $CO_2$. (Of course, in the case of various catalysts, the mechanism of hydrogenation of bicarbonate and hydrated carbon dioxide, especially when both substrates are present together, can be significantly different.)

The situation is complicated if, under the given conditions, a rapid exchange process takes place between the dissolved $CO_2$ (or the resulting $H_2CO_3$) and $HCO_3^-$. In that case, it is not possible to decide whether, in addition to the hydrogen carbonate, the (hydrated) $CO_2$ dissolved in the reaction mixture also reacts independently or whether the reactant is only the $HCO_3^-$ formed during the rapid exchange. Most of the literature reports do not even pay attention to this possibility: they consider the process as "$CO_2$-hydrogenation" even when the originally introduced $NaHCO_3$ did not react to 100%, i.e. all of the formed formate could have come from hydrogen carbonate without that hydrated $CO_2$ would have reacted with hydrogen. However, if 100% of the originally introduced $HCO_3$ is converted into formate, then the amount of formate (formic acid) that exceeds this is necessarily formed from the $CO_2$ that was originally in the gas phase. Of course, in the presence of basic auxiliary materials, e.g. amines, the $CO_2$ in the gas phase is also reduced, since it gives a bicarbonate (possibly carbonate) salt with the base, which is known to be hydrogenable. In such cases, however, according to experimental experience, the amount of the base present determines the maximum achievable formate concentration.

The inventors of the present invention believe that for a clear answer, the exchange process indicated in the previous paragraph, or—with isotopic labeling—the examination of the isotope ratio formed in the formate obtained as a product, primarily with mass spectrometry methods, would be necessary. However, the following observations deserve consideration.

a) In the publications [2]-[4] mentioned several times above, the reactions were carried out in high-pressure NMR tubes, and was followed by $^1H$ or $^{13}C$ NMR spectroscopy using $NaH^{13}CO_3$, an isotopically labeled Na-bicarbonate starting material. During the reaction, the $^1H$ and $^{13}C$ measurements clearly showed the increase in formate concentration over time, which was determined quantitatively from the ratio of the formate $HCO_2^-$ proton signal intensity to the corresponding internal standard (DSS) proton signal intensity. The conversion of the starting material and the final formate concentration were calculated based on these data. With this method, it is not possible to distinguish whether the detected formate was formed from bicarbonate or hydrated $CO_2$.

In other cases (such as in the above-mentioned publication [1]), the formate concentration formed was determined by HPLC measurements, using elution with an acidic medium. The latter method does not differentiate between formate and formic acid, either, because formate is also protonated in the eluent used and can be detected as formic acid.

b) The $HCO_3^-$ anion can also be hydrogenated without $CO_2$ in an aqueous solution. On the other hand, knowing that in the absence of $HCO_3^-$, i.e. when the aqueous solution containing only the catalyst is placed under a $H_2/CO_2$ gas mixture, even at high pressure and temperature, only a negligible amount of formic acid is formed (see e.g. [1]), it seems obvious to assume that the $HCO_3^-$ hydrogenates at a much higher rate than hydrated $CO_2$ (ie, bicarbonate is the substrate for hydrogenation).

c) We mentioned earlier that in the presence of bases, $CO_2$ introduced in the gas phase is also hydrogenated, since with the base it gives a bicarbonate (possibly carbonate) salt, which is known to be hydrogenable. In such cases, however, according to experimental experience, the amount of base present (KOH, NaOH, dimethylamine, etc.) determines the maximum achievable formate concentration.

d) Some catalysts break formic acid ($HCO_2H$) into hydrogen and carbon dioxide at an extremely high rate. Of course, this process only takes place in an acidic medium where the formic acid does not predominantly dissociate, because otherwise it would be dehydrogenation of the formate anion. In purely aqueous solutions (i.e. in the absence of $NaHCO_3$), the low final concentration of the formic acid formed in the reaction $CO_2+H_2=HCO_2H$ may also be the result of the fact that the catalyst also breaks down the product and the balance is strongly shifted in the direction of the starting materials.

Based on the data published in the already mentioned publication [4] by Laurenczy et al., the final formate concentrations contain significant concentration data (1.53 M and 1.70 M), but in no reaction did the concentration of the formed $HCO_2$ exceed the measured $NaHCO_3$ or $KHCO_3$ concentration in the used 1-50 bar $CO_2$ pressure range. Assuming that formate was formed solely by hydrogenation of the input $KHCO_3$, the maximum bicarbonate conversion was 85%. These observations clearly indicate that the $CO_2$ present in the $H_2/CO_2$ mixtures has primarily a kinetic effect on the hydrogenation of hydrogen carbonate. The details of this have not been revealed in the studies so far, but the decrease in the pH of bicarbonate solutions due to the effect of dissolved $CO_2$ may influence the formation of catalytically active metal complex particles (almost certainly hydrido-complexes). However, there are limits to the pH reduction, as can be seen from reference table 1 above. However, the direct self-hydrogenation of dissolved CO2 does not significantly contribute to the amount of formate formed. In this sense, it is not a reactant (substrate) of hydrogenation, and the Le Chatelier-Braun principle cannot be applied to it, according to which increasing the concentration of the reactant(s) favors the formation of products. It is well known that the Le Chatelier-Braun principle is a clearly formulated thermodynamic law, but it does not say anything about the kinetics of the given reaction.

U.S. Pat. No. 4,067,958 patent discloses a process for producing hydrogen from fuel gas containing carbon monoxide and other components. The fuel gas is passed through an aqueous solution containing sodium and potassium carbonate and/or bicarbonate while the corresponding formate is formed. The formate solution is then catalytically decomposed to produce hydrogen and carbonate and/or bicarbonate. The cited patent document also presents the equipment implementing the procedure. The catalysts used can be transition metals, their oxides or sulfides on a support resistant to alkalis.

Laurenczy et al. (Inorg. Chem. Comm. 2007, 10, 558-562) published a Ru(II) complex, namely the [RuCl$_2$(PTA) ([9]aneS$_3$)] complex (where PTA is 1.3, 5-triaza-7-phosphadamantane and [9]aneS3 is 1,4,7-trithiacyclononane), which can catalyze the hydrogenation of carbon dioxide and bicarbonates in an aqueous medium. In the publication, it is stated that although the catalytic activity is very modest, the presence of intermediate products appearing during the reaction, suggested by previous theoretical and practical results, has been undoubtedly proven.

In US20120321550 patent document, Fukuzumi et al. disclose in great detail mononuclear transition metal complexes (including stereoisomers) that can be used in hydrogen storage processes (starting from Y. Himeda's previous work). In their case, hydrogen is produced from alcohols, and then the starting alcohol is recovered from the formed aldehyde by hydrogenation with a similar catalyst. Furthermore, the $HCOOH/HCOO^-/CO_2/HCO_3^-$ balance is successfully used in these systems. In their case, the pH in the given system is also a key issue, also in connection with the pH sensitivity of the ligand. Although the formate/hydrocarbonate cycle plays a role in the systems described in the referenced patent document, the family of catalysts used has a different structure than that disclosed in the present invention, and does not contain either N-heterocyclic (hereafter sometimes: NHC) carbene or phosphine.

Mahajan summarizes his experiments in formate decomposition (sodium, potassium, lithium and cesium formate) catalyzed by transition metal complexes in U.S. Pat. No. 6,596,423 patent document. Conducting the reaction according to the described procedure (at a temperature in the range of 80-150° C.), the reaction product also contains traces of carbon monoxide (less than 50 ppm). The patent document mentions several possible complexing metals, including iridium. Possible catalysts can be transition metal carbonyl complexes or ligand-coordinating complexes containing an N-donor group (for example, a 2,2'-dipyridyl group). It also provides several options for the reaction medium, such as water or methanol.

In patent application No. DE102006030449, a device suitable for reversible hydrogen storage is disclosed. The basis of the operation of the equipment is the binding of hydrogen and its release. Hydrogen is bound by reducing potassium carbonate and/or potassium bicarbonate in aqueous solution to potassium formate with an electric current in the presence of hydrogen gas and a ZnO or ZnO\TiO$_2$ catalyst. Hydrogen is released from an aqueous solution of potassium formate, formic acid or their mixture using platinum or palladium catalysts. Note that not the same catalyst is used for hydrogen storage and hydrogen release.

U.S. Pat. No. 7,939,461 discloses metal complexes that catalyze the decomposition of formic acid with hydrogen formation. The application also discloses the theoretical possibility of a device that enables the storage and recovery of hydrogen produced during the decomposition of formic acid. The disclosed metal complexes contain two transition metal ions (binuclear complexes), which may be identical or different. In the description of the invention, iridium is included among the possible metal atoms. Possible ligands in substituted or unsubstituted form are cyclopentadiene, N-atom-containing heterocyclic aromatic compounds, such as bipyridine, phenanthroline, bipyrimidine. In the given examples, the production of a water-soluble iridium-ruthenium complex and the decomposition of formic acid with the formation of hydrogen and carbon dioxide under various conditions (different temperatures and pH) are presented. The description also presents complexes (for example containing iridium) that catalyze the formation of formic acid from hydrogen and carbon dioxide. The catalysts disclosed in the referenced patent document have a different structure than the complex catalysts disclosed in the present invention, so for example they do not contain phosphine ligands.

In a publication by Beller and his research group (Tetrahedron Lett. 2009, 50, 1603-1606), it was described how hydrogen production from formic acid with a Ru-containing catalyst can be influenced by adding organic bases and inorganic salts to the catalyst system. It has been demonstrated that the presence of amidine compounds increases hydrogen production, and under optimal conditions, hydrogen can be efficiently produced from a formic acid/amine mixture. The catalyst system proved to be most effective in the presence of 1,2-bis-(diphenylphosphino)ethane (dppe) and N,N-dimethyl-n-hexylamine in the case of $[RuCl_2(benzene)]_2$ precursor.

Patent document No. WO2012143372 presents a process by which hydrogen can be produced from formic acid by selective dehydration using a catalyst system containing transition metal complexes coordinating at least one tetradentate ligand. Although iridium is also mentioned among the possible transition metals, ruthenium, cobalt and iron are included in the disclosed preferred embodiments of the invention. The description mentions phosphine ligands, but carbene complexes of transition metals are not mentioned as precursors.

Joó et al. [Angew. Chem. Int. Ed. 2011, 50, 10433-10435 (hereinafter: own research results)] also investigated the possibilities of using the formate/hydrocarbonate cycle. The catalyst described here is the Ru(II)-mtppms-complex, from which Ru-formate dihydride is formed during the reaction, which specifically performs the decomposition. The chemical storage of $H_2$ in formate was achieved within one system, since at the applied temperature, in the presence of the Ru(II)-mtppms catalyst, the formate decomposes (no $CO_2$ emissions), while after the decomposition is completed, the initial formate solution can be recovered by filling the formed $HCO_3^-$ and catalyst solution with relatively high pressure $H_2$. It was possible to complete the cycle several times in a row. Although the formate/hydrocarbonate cycle plays a role in the systems described in the publications, the catalyst is a Ru(II) complex, and complexes of iridium or other transition metals are not mentioned, and the use of NHC carbene as a ligand does not arise.

Himeda (Green Chem. 2009, 11, 2018-2022) investigated the decomposition of formic acid in an aqueous medium in the presence of an iridium catalyst. The resulting hydrogen did not contain carbon monoxide. 4,4'-dihydroxy-2,2'-bipyridine was present as a ligand. Based on the results, the Ir-bipyridyl complexes proved to be very active catalysts. At 90° C., the catalytic activity was TOF-14000 h$^{-1}$. The author also investigated the effect of formate on the decomposition of formic acid. He found that this catalyst is also active in the decomposition of HCOOH/HCOO$^-$ mixtures. Furthermore, on a theoretical-principle level, he predicted that the aqueous solution of the $CO_2$ formed ($HCO_3^-$ solution) can be rehydrogenated and that formic acid is formed again by lowering the pH. He also proposed the mechanism of the reaction taking place, in which he identified the catalytically active intermediate as Ir-hydride.

Using a similar Ir catalyst, also Himeda et al solved the rehydrogenation of $CO_2$ formed from the decomposition of formic acid by changing its pH within a single system (Nature Chem. 2012, 4, 383-388). The catalyst they use (through the pH sensitivity of the ligand) catalyzes the decomposition of formic acid in an acidic pH range, while the reduction of $CO_2$ comes to the fore in alkaline solutions. According to their suggestion, $H_2$ can be stored reversibly in formate solutions.

Although the formate/hydrocarbonate cycle also appears in the two aforementioned publications, but the catalyst used does not contain either NHC carbene or phosphine, during the decomposition the pH is in the acidic range, i.e. the formic acid decomposes ($CO_2$ is also formed), and the pH must be increased in order for the reduction process to start, in contrast to our system, where the pH does not change significantly.

Nolan et al. in U.S. Pat. No. 6,774,274 patent document disclose complexes of formula [Ir(cod)(N)(L)]X, which were prepared by reaction of [Ir(cod)(py)$_2$]PF$_6$ (where cod is 1,5-cyclooctadiene, py and meaning pyridine) and L or together with N and L ligands. The use of said catalysts in the hydrogenation of olefins is also disclosed. The preparation of the complex according to formula [Ir(cod)(py)(SIMes)]PF$_6$ (where SIMes is 1,3-dimesityl-4,5-dihydroimidazol-2-ylidene or a related N-heterocyclic carbene) and its main features are demonstrated. In the referenced patent document, nucleophile-type N-heterocyclic carbenes are mentioned as an alternative to phosphine ligands, which are widespread in homogeneous catalysis, emphasizing the general experimental experience that using N-heterocyclic carbene ligands with more favorable steric and/or electronic characteristics instead of phosphine ligands, a significant catalytic performance increase can be achieved in the case of olefins. The patent document does not disclose catalysts containing a mixture of NHC carbene and phosphine ligands, and in addition offers a solution to a fundamentally different technical problem.

In their publication (Angew. Chem. Int. Ed. 2008, 47, 3966-3968), Laurenczy et al. present an efficient, selective system suitable for hydrogen evolution from an aqueous solution of formic acid in the presence of a water-soluble, in situ produced catalyst. [Ru(II)(H$_2$O)$_6$](tos)$_2$]-complex, where tos means toluyl-4-sulfonate and RuCl$_3$, were used as precursors, and meta-trisulfonated triphenylphosphine (mtppts) as ligand. Sodium formate was added to the solution to activate the catalyst.

In another publication (ChemCatChem 2013), Laurenczy et al. investigated the catalytic decomposition of a HCOOH/HCOO$^-$ mixture in the presence of a water-soluble catalyst containing Ru-ions, where the ligands forming the complex were cationic triarylphosphine derivatives substituted with one or more trimethylammonium groups. Optimization experiments were also carried out with the most promising precursor, during which, among other things, the effect of pH, temperature, catalyst concentration and ligand/Ru ratio were investigated. The catalytic cycle number achieved under optimal conditions was TOF=1950 h$^{-1}$.

In the publications listed above, the catalyst system is ruthenium-based and contains though various phosphine ligands, but there is no mention of NHC carbenes as possible ligands.

Patent document WO2008047312 by Laurenczy et al. refers to a process by which hydrogen and carbon dioxide can be produced in an aqueous medium from formic acid by a catalytic method, without the generation of carbon monoxide. The catalyzed process takes place in a wide temperature range and at room temperature (T=25° C.). The patent document also mentions iridium as a transition metal, the complexes of which may be suitable as catalysts in the investigated processes, but no relevant experimental results are presented. In preferred embodiments of the invention, iridium is not included. Among the possible ligands of transition metal complex catalysts, it mentions phosphines, preferably aromatic phosphines, specifically mtppts and mtppms ligands, and carbenes. However, the document does not give a specific example of the latter. The patent document does not state that the carbon dioxide or $HCO_3^-$ solution formed during decomposition would be converted back into formic acid or formate solution.

U.S. Pat. No. 8,133,464 patent document by Laurenczy et al. also relates to the decomposition of various formic acid/formate mixtures into hydrogen and carbon dioxide. Compared to their previous patent (WO2008047312), the range of catalysts used has been widened. The patent document discloses a complex with the composition M(L)n, where M is preferably Ru and Rh, but can also be Ir. Several variations of L as a ligand are claimed, where L can be a sulfonated phosphine and/or carbene and/or a hydrophilic group and combinations thereof. However, this patent document does not provide a clear range of possible carbenes as ligands either.

U.S. Pat. No. 10,944,119B2 discloses a process that enables the storage and release of hydrogen. Although the document mentions the bicarbonate-formate cycle in relation to the storage and release of hydrogen, however, during the release of hydrogen, the used transition metal catalyst (ruthenium-containing complex) is dissolved in an organic solvent or solvent mixture, and the resulting bicarbonate is formed in the aqueous phase separated from the organic solution containing the catalyst. So much has been revealed about the hydrogenation of bicarbonate that this step can also be facilitated by the same catalyst system as the decomposition of formate.

Chinese patent document No. CN105283436B discloses a process for producing formic acid from hydrogen gas and carbon dioxide in the presence of a catalyst. The process is carried out in an acidic medium containing a polar solvent (e.g. water or DMSO) and no base, carbonate, bicarbonate or formate is added.

US patent document US20150105571A1 discloses a process for converting carbon dioxide or bicarbonate into a formic acid derivative (e.g. formate salt, formate ester and formamide) using a catalyst system containing molecular hydrogen and cobalt complex.

Based on the state of the art, it can be established that the effect of $CO_2$ on the hydrogenation of bicarbonate with various catalysts can be either speed-increasing or speed-decreasing, and the extent cannot be determined based on prior knowledge. Based on the research results and experience summarized above, the creators of the present invention believe that the actual substrate of $CO_2$ hydrogenation is the $HCO_3^-$ anion. Its concentration naturally increases with $CO_2$ pressure, but not linearly, as Henry's law would require (even in small pressure ranges).

THE PROBLEM TO BE SOLVED BY THE INVENTION

Figure 1:
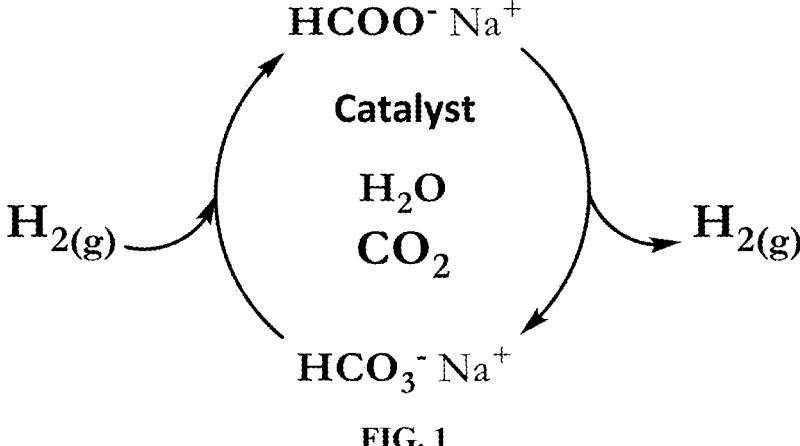
FIG. 1: A catalytic cycle suitable for storing and releasing hydrogen, where the hydrogenation of hydrogen carbonate ($HCO_3^-$) is carried out in the presence of carbon dioxide ($CO_2$) in the gas space.

The technical problem to be solved with the invention is to provide a reaction system suitable for the reversible storage of hydrogen gas that can be used in fuel cells or other equipment requiring $H_2$, which enables the production of hydrogen gas ($H_2$) free of $CO_x$ by-products by breaking down formates in an aqueous reaction system, as well as the hydrogenation of hydrogen carbonates produced in the same reaction system using the same catalyst in such a way, that the activity of the catalyst in the hydrogenation step of hydrogen carbonates is greater than the activity of the catalysts in the previously known hydrogenation process of hydrogen carbonates.

DISCOVERY ACCORDING TO THE INVENTION

Our invention achieves the mentioned goals with a solution based on the surprising discovery that if the hydrogenation of hydrogen carbonates is carried out in an aqueous reaction system with carbon dioxide present in the gas space, the activity of the catalyst according to the invention will be up to six times higher—the depending on the conditions used (properly chosen pressure and temperature)—as in the case of hydrogenation of hydrogen carbonates in an aqueous reaction system with pure hydrogen.

BRIEF DESCRIPTION OF THE INVENTION

1. A process for the hydrogenation of hydrogen carbonate ($HCO_3^-$), in an aqueous reaction system, preferably said hydrogen carbonate being selected from sodium hydrogen carbonate ($NaHCO_3$), lithium hydrogen carbonate ($LiHCO_3$), cesium hydrogen carbonate ($CsHCO_3$) and potassium hydrogen carbonate ($KHCO_3$) and for the production of formate, preferably formate selected from the group of sodium formate (HCOONa), lithium formate (HCOOLi), cesium formate (HCOOCs) and potassium formate (HCOOK), said process comprising bringing said hydrogen carbonate and a catalyst into contact with each other at an elevated temperature, preferably at 60-100° C., more preferably at 80° C., at a pressure of 1-1200 bar, preferably 10-100 bar;

where the catalyst is a catalyst with the general formula [Ir(cod)(NHC)P$_a$]+nP$_b$, where in the formula Ir is iridium;

cod is 1,5-cyclooctadiene;

NHC is an N-heterocyclic carbene, preferably 1-R-3-methylimidazol-2-ylidene, where R is C1-C6 alkyl or benzyl;

n is an integer from 1 to 4; and $P_a$ and $P_b$ are independently 1,3,5-triaza-7-phosphadamantane (pta), monosulfonated triphenylphosphine (mtppms) or trisulfonated triphenylphosphine (mtppts);

wherein the hydrogenation of hydrogen carbonate is carried out in such a way that carbon dioxide is present in the gas space.

2. The process according to Point 1, wherein the catalyst used is selected from the following:

a) a catalyst according to the formula [Ir(emim)(cod)(mtppms]+mtppts, wherein emim is 1-ethyl-3-methyl-imidazol-2-ilydene, cod is 1,5-cyclooctadiene, mtppms is monosulfonated triphenylphosphine and mtppts is trisulfonated triphenylphosphine;

b) a catalyst according to the formula [Ir(bmim)(cod)(mtppms]+mtppts, wherein bmim is 1-butyl-3-methyl-imidazol-2-ilydene, cod is 1,5-cyclooctadiene, mtppms is monosulfonated triphenylphosphine and mtppts is trisulfonated triphenylphosphine;

c) a catalyst according to the formula [Ir(hexmim)(cod)(mtppms]+mtppts, wherein hexmim is 1-hexyl-3-methylimidazol-2-ilydene, cod is 1,5-cyclooctadiene, mtppms is monosulfonated triphenylphosphine and mtppts is trisulfonated triphenylphosphine;

d) a catalyst according to the formula [Ir(2mim)(cod)(mtppms]+mtppts, wherein 2mim is 1,3-dimethyl-imidazol-2-ilydene, cod is 1,5-cyclooctadiene, mtppms is monosulfonated triphenylphosphine and mtppts is trisulfonated triphenylphosphine;

e) a catalyst according to the formula [Ir(Bnmim)(cod)(mtppms]+mtppts, wherein Bnmim is 1-benzyl-3-methylimidazol-2-ilydene, cod is 1,5-cyclooctadiene, mtppms is monosulfonated triphenylphosphine and mtppts is trisulfonated triphenylphosphine;

f) a catalyst according to the formula [Ir(emim)(cod)(mtppms]+pta, wherein emim is 1-ethyl-3-methylimidazol-2-ilydene, cod is 1,5-cyclooctadiene, mtppms is monosulfonated triphenylphosphine and pta is 1,3,5-triaza-7-phosphadamantane; and g) a catalyst according to the formula [Ir(emim)(cod)(mtppms]+mtppms, wherein emim is 1-ethyl-3-methylimidazol-2-ilydene, cod is 1,5-cyclooctadiene, mtppms is monosulfonated triphenylphosphine.

3. A process for decomposing a formate, preferably a formate selected from sodium formate (HCOONa), lithium formate (HCOOLi), cesium formate (HCOOCs) and potassium formate (HCOOK) in an aqueous reaction system and for producing hydrogen gas ($H_2$) free of $CO_x$ by-products, and in the same reaction system, for the hydrogenation of the resulting hydrogen carbonate ($HCO_3^-$), preferably a hydrogen carbonate selected from the group of sodium hydrogen carbonate ($NaHCO_3$), lithium hydrogen carbonate ($LiHCO_3$), cesium hydrogen carbonate ($CsHCO_3$) and potassium hydrogen carbonate ($KHCO_3$) in an aqueous reaction system, thus for the production of a formate, preferably a formate selected from the group of sodium formate (HCOONa), lithium formate (HCOOLi), cesium formate (HCOOCs) and potassium formate (HCOOK);

where the reactants and the reaction products are formed in a reversible reaction cycle by using the reaction system of the formate decomposition step and the bicarbonate hydrogenation step and by choosing the values of temperature, pressure and pH within the ranges specified below, and this reaction cycle is repeated the required number of times;

where the formate decomposition step includes bringing the formate into contact with the catalyst in an aqueous reaction system, at an elevated temperature, preferably at 60-100° C., preferably at 80° C., preferably at a pH greater than 8, preferably at a pH=8.3±0.2, in an Ar gas atmosphere;

where the hydrogenation step of the hydrogen carbonate includes bringing the hydrogen carbonate and a catalyst into contact with each other, at an elevated temperature, preferably at 60-100° C., more preferably at 80° C., under pressure of 1-1200 bar, preferably 10-100 bar;

where the catalyst is a catalyst with the general formula $[Ir(cod)(NHC)P_a]+nP_b$, where in the formula Ir is iridium;

cod is 1,5-cyclooctadiene;

NHC is an N-heterocyclic carbene, preferably 1-R-3-methylimidazol-2-ylidene, where R is C1-C6 alkyl or benzyl;

n is an integer from 1 to 4; and $P_a$ and $P_b$ mean independently a 1,3,5-triaza-7-phosphadamantane (pta), monosulfonated triphenylphosphine (mtppms) or trisulfonated triphenylphosphine (mtppts);

according to which the hydrogenation of hydrogen carbonate is carried out in such a way that carbon dioxide is present in the gas space.

4. The process according to Point 3, according to which the catalyst used is selected from the following:

a) a catalyst according to the general formula [Ir(emim)(cod)(mtppms]+mtppts, where emim is 1-ethyl-3-methylimidazol-2-ilydene, cod means 1,5-cyclooctadiene, mtppms is monosulfonated triphenylphosphine and mtppts is trisulfonated triphenylphosphine;

b) a catalyst according to the general formula [Ir(bmim)(cod)(mtppms]+mtppts, where bmim is 1-butyl-3-methylimidazol-2-ilydene, cod is 1,5-cyclooctadiene, $_m$tppms is monosulfonated triphenylphosphine and $_m$tppts is trisulfonated triphenylphosphine;

c) a catalyst according to the general formula [Ir(hexmim)(cod)(mtppms]+mtppts, where hexmim is 1-hexyl-3-methylimidazol-2-ilydene, cod is 1,5-cyclooctadiene, mtppms is monosulfonated triphenylphosphine and mtppts is trisulfonated triphenylphosphine;

d) a catalyst according to the general formula [Ir(2mim)(cod)(mtppms]+mtppts, where 2mim is 1,3-dimethyl-imidazol-2-ilydene, cod is 1,5-cyclooctadiene, mtppms is monosulfonated triphenylphosphine and mtppts is trisulfonated triphenylphosphine;

e) a catalyst according to the general formula [Ir(Bnmim)(cod)(mtppms]+mtppts, where Bnmim is 1-benzyl-3-methylimidazol-2-ilydene, cod is 1,5-cyclooctadiene, mtppms is monosulfonated triphenylphosphine and mtppts is trisulfonated triphenylphosphine;

f) a catalyst according to the general formula [Ir(emim)(cod)(mtppms]+pta, where emim is 1-ethyl-3-methyl-imidazol-2-ilydene, cod is 1,5-cyclooctadiene, mtppms is monosulfonated triphenylphosphine and pta is 1,3,5-triaza-7-phosphadamantane; and g) a catalyst according to the general formula [Ir(emim)(cod)(mtppms]+mtppms, where emim is 1-ethyl-3-methylimidazol-2-ilydene, cod is 1,5-cyclooctadiene, mtppms is monosulfonated triphenylphosphine.

5. Use of the process according to Point 3 for a hydrogen storage system.

6. The hydrogen storage system according to Point 4, which is a hydrogen battery.

7. Use of the hydrogen storage system according to Point 5 or 6 for storing the hydrogen required to operate a fuel cell or other equipment requiring $H_2$, and optionally for releasing thereof to the extent of necessary.

DETAILED DESCRIPTION OF THE INVENTION

In the course of our work, we developed a process for the hydrogenation of hydrogen carbonate ($HCO_3^-$) in an aqueous reaction system in the presence of a catalyst, where the process includes bringing the aforementioned hydrogen carbonate, hydrogen and catalyst into contact with each other in such a way that carbon dioxide is present in the gas space, thus formate ($HCOO^-$) is produced.

In the course of our work, we came to the surprising discovery that if the hydrogenation of hydrogen carbonate in an aqueous reaction system is carried out in such a way that carbon dioxide is present in the gas space, then the activity of the catalyst according to the invention will be up to six times higher—depending on the applied pressure and temperature —, than in the case of hydrogenation of hydrogen carbonate in an aqueous reaction system with pure hydrogen.

Based on the above, the first aspect of our invention is to provide a process for the hydrogenation of a hydrogen carbonate ($HCO_3^-$), preferably sodium hydrogencarbonate ($NaHCO_3$), lithium hydrogencarbonate ($LiHCO_3$), cesium hydrogencarbonate ($CsHCO_3$) or potassium hydrogencarbonate ($KHCO_3$) in an aqueous reaction system in the presence of carbon dioxide in the gas space, and for the production of a formate, preferably sodium formate ($HCOONa$), lithium formate ($HCOOLi$), cesium formate ($HCOOCs$) or potassium formate ($HCOOK$), where the hydrogen carbonate and the catalyst are brought into contact with each other at an elevated temperature, preferably at 60-100° C., more preferably at 80° C., at a pressure of 1-1200 bar, preferably 10-100 bar.

In one embodiment of the invention, the amount of $CO_2$ present in the gas space during the contact between said hydrogen carbonate and the catalyst is: $p(CO_2)>0$ bar and $p(CO_2)\leq50$ bar.

The mentioned catalyst is a catalyst of the general formula $[Ir(cod)(NHC)P_a]+nP_b$, which is suitable for the decomposition of formates in an aqueous reaction system and the production of hydrogen gas ($H_2$) free of $CO_x$ by-products, or for the hydrogenation of hydrogen carbonates ($HCO_3^-$), where in the formula Ir is iridium, cod is 1,5-cyclooctadiene and NHC is an N-heterocyclic carbene, preferably 1-R-3-methylimidazol-2-ylidene, where R is C1-C6 alkyl or benzyl, $P_a$ and $P_b$ independently of each other are 1,3,5-triaza-7-phosphadamantane (pta), monosulfonated triphenylphosphine (mtppms) or trisulfonated triphenylphosphine (mtppts), and n is an integer from 1 to 4.

If the catalytic hydrogenation of bicarbonate into formate according to the invention and the catalytic decomposition of formate into bicarbonate are combined in such a way that the mentioned steps are carried out in the same reaction system, in an aqueous medium, in the presence of a water-soluble catalyst, i.e. the reactants and reaction products are formed in a reversible reaction cycle, then we can create a hydrogen storage system.

Based on the above, a further aspect of our invention is to provide a process for the decomposition of formate, preferably sodium formate ($HCOONa$), lithium formate ($HCOOLi$), cesium formate ($HCOOCs$) or potassium formate ($HCOOK$) in an aqueous reaction system and for the production of hydrogen gas ($H_2$) free of $CO_x$ by-products, and for the hydrogenation of a hydrogen carbonate ($HCO_3^-$), preferably sodium hydrogen carbonate ($NaHCO_3$), lithium hydrogen carbonate ($LiHCO_3$), cesium hydrogen carbonate ($CsHCO_3$) or potassium hydrogen carbonate ($KHCO_3$), produced in the same reaction system, in an aqueous reaction system in the presence of carbon dioxide in the gas space to produce formate, preferably sodium formate ($HCOONa$), lithium formate ($HCOOLi$), cesium formate ($HCOOCs$) or potassium formate ($HCOOK$), where using the reaction system of the process for decomposing of formate and for hydrogenating hydrogen carbonate according to the invention, and by choosing the reaction conditions, such as temperature, pressure and pH, within the ranges given below, the reactants and reaction products are formed in a reversible reaction cycle, and this reaction cycle is repeated in the required number of times.

In the mentioned process, the formate decomposition step is carried out by bringing the formate, preferably sodium formate ($HCOONa$), lithium formate ($HCOOLi$), cesium formate ($HCOOCs$) or potassium formate ($HCOOK$) into contact with the catalyst in an aqueous reaction system at an elevated temperature, preferably at 60-100° C., preferably at 80° C., preferably at a pH greater than 8, preferably at a pH=8.3±0.2, in an Ar gas atmosphere.

A further aspect of our invention is a hydrogen storage system that includes the components described above in the invention. The hydrogen storage system according to the invention is preferably a hydrogen accumulator.

Another aspect of the invention is the use of the hydrogen storage system according to the invention to store the hydrogen required for the operation of a fuel cell (or other equipment requiring $H_2$) and, where applicable, to release it as needed.

In the following, our invention is illustrated with examples for a better understanding, which, however, we do not intend to interpret as a limitation of the invention.

EXAMPLES

Example 1: Examining the Change in pH in $NaHCO_3$ Solution as a Function of $CO_2$ Pressure We investigated the change of pH in a 0.1 M $NaHCO_3$ solution at a temperature of 80° C. as a function of the applied $CO_2$ pressure (Xiaolu Li, Cheng Peng, John P. Crawshaw, Geoffrey C. Maitland, J. P. Martin Trusler, Fluid Phase Equilibria, 2018, 458, 253-263).

Figure 2:
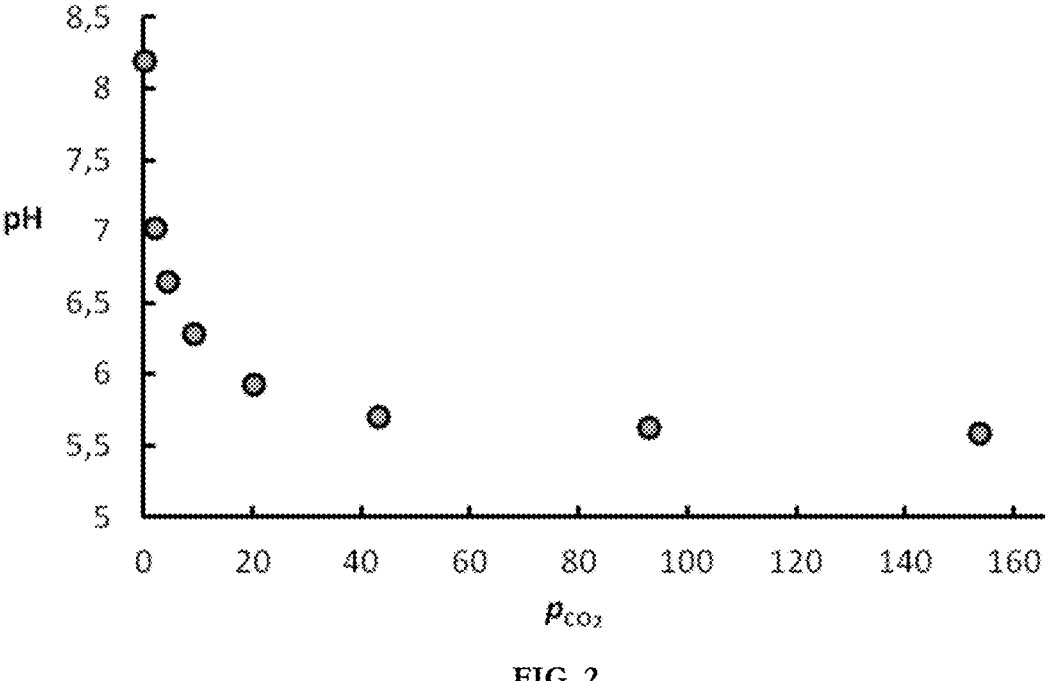
FIG. 2: The change in pH with increasing $CO_2$ pressure in 0.1 M $NaHCO_3$ solution at 80° C.

The change in pH as a function of the $CO_2$ pressure can be seen in FIG. 2, from which it can be clearly read that the pH of the solution shifts in an acidic direction as the $CO_2$ pressure increases, however, the change is not linear—even a small amount of carbon dioxide causes a significant degree of acidification. It can be concluded that by using the highest $CO_2$ pressure (50 bar) that we used, the pH practically drops from 8.2 to 5.7.

Example 2: Investigation of the Effect of $CO_2$ on the Activity of the $[Ir(Emim)(Cod)(Mtppms]+Mtppts$ Catalyst The general formula of the tested catalyst is $[Ir(emim)(cod)(mtppms]+mtppts$, where emim is 1-ethyl-3-methylimidazol-2-ylidene, cod is 1,5-cyclooctadiene, mtppms is monosulfonated triphenylphosphine and mtppts is triple sulfonated triphenylphosphine.

Reaction mixture: in a 100.0 mL constant temperature batch reactor (100 mL Series 5500 HP Compact Reactor manufactured by Parr Instruments):

20.0 ml solution volume,
80° C.,
$[Ir]=0.0005$ mol/dm$^3$,
$[mtppms]=[Ir]$,
$[mtppts]=0,001$ mol/dm$^3$,
$[HCO_3Na]=0.1$ mol/dm$^3$,
$p(H_2)=50$ bar,
$p(CO_2)=$varied in the range of 0-50 bar,
reaction time=1 hour.

In summary, we found that by varying the $CO_2$ pressure between 0 and 50 bar (under the reaction conditions used), the achieved TON value increases from 121 to 213, which means an almost two-fold increase in reaction rate. The formate concentration in the solution obtained after a reaction time of 1 hour without the use of $CO_2$ is $[HCO_2^-]_0=60.5$ mM, and in a 50 bar $CO_2$ atmosphere $[HCO_2^-]_{50}=106.5$ mM. From this, a total of 2.13 mmol $HCO_2$ was formed in an atmosphere of 50 bar $CO_2$, which is only 6.5% more than the originally measured amount of bicarbonate (2 mmol). The obtained measurement results are shown in FIG. 3.

Figure 3:
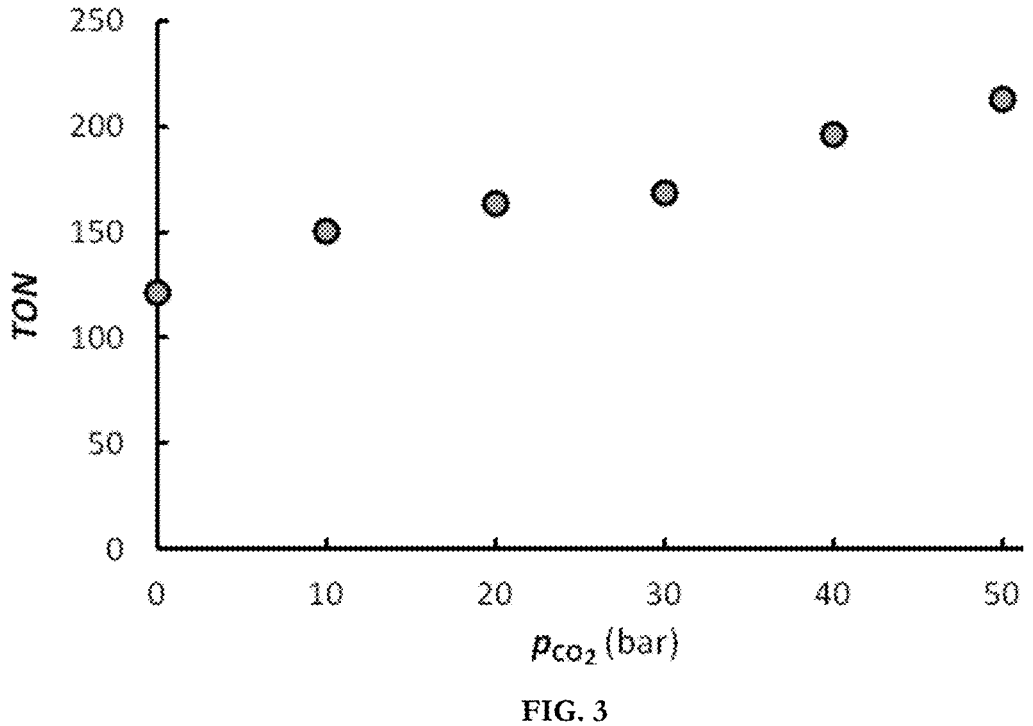
FIG. 3: The change of the catalytic cycle number (Turn-Over Number, hereinafter: TON) depending on the applied $CO_2$ pressure using [Ir(emim)(cod)(mtppms]+mtppts catalyst in a batch reactor with a total volume of 100 ml.
Figure 4:
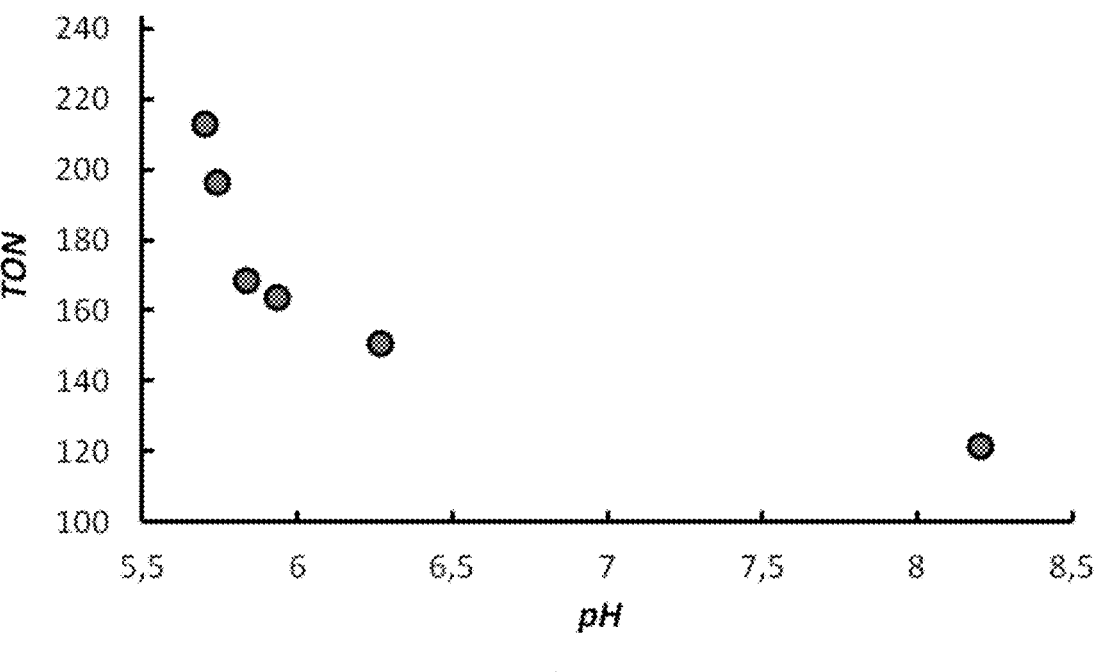
FIG. 4: The change of the catalytic cycle number (TON) values as a function of pH using [Ir(emim)(cod)(mtppms]+mtppts catalyst in a batch reactor with a total volume of 100 ml.

From the data in FIG. 3, we determined the change in the catalytic cycle number as a function of pH using the data in FIG. 2 presented in Example 1 (change in pH with increasing CO2 pressure). The obtained results are shown in FIG. 4.

Example 3: Investigation of the Effect of $CO_2$ on the Activity of the [Ir(Emim)(Cod)(Mtppms]+Mtppts Catalyst Reaction mixture: in a 600.0 ml constant temperature batch reactor (600 ml Series 5500 HP Compact Reactor manufactured by Parr Instruments):

200.0 ml solution volume,
80° C.,
$[Ir]=0.00005$ mol/dm$^3$,
$[mtppms]=[Ir]$,
$[mtppts]=0.0001$ mol/dm$^3$,
$[HCO_3Na]=0.1$ mol/dm$^3$
$p(H_2)=50$ bar,
$p(CO_2)=$varied in the range of 0-50 bar,
reaction time=1 hour.

In summary, we found that by varying the $CO_2$ pressure between 0 and 50 bar (under the reaction conditions used), the achieved TON value increases from 260 to 576, which means a more than two-fold increase in speed. The formate concentration in the solution obtained after a reaction time of 1 hour without the use of $CO_2$ is $HCO_2^-]_0=13.0$ mM, and in a 50 bar $CO_2$ atmosphere $[HCO_2^-]_{50}=28.8$ mM. In other words, the resulting formate concentration does not approach the measured bicarbonate concentration (100.0 mM) in any case, the maximum degree of bicarbonate conversion (conversion) is 28.8%. The obtained measurement results are shown in FIG. 5.

Figure 5:
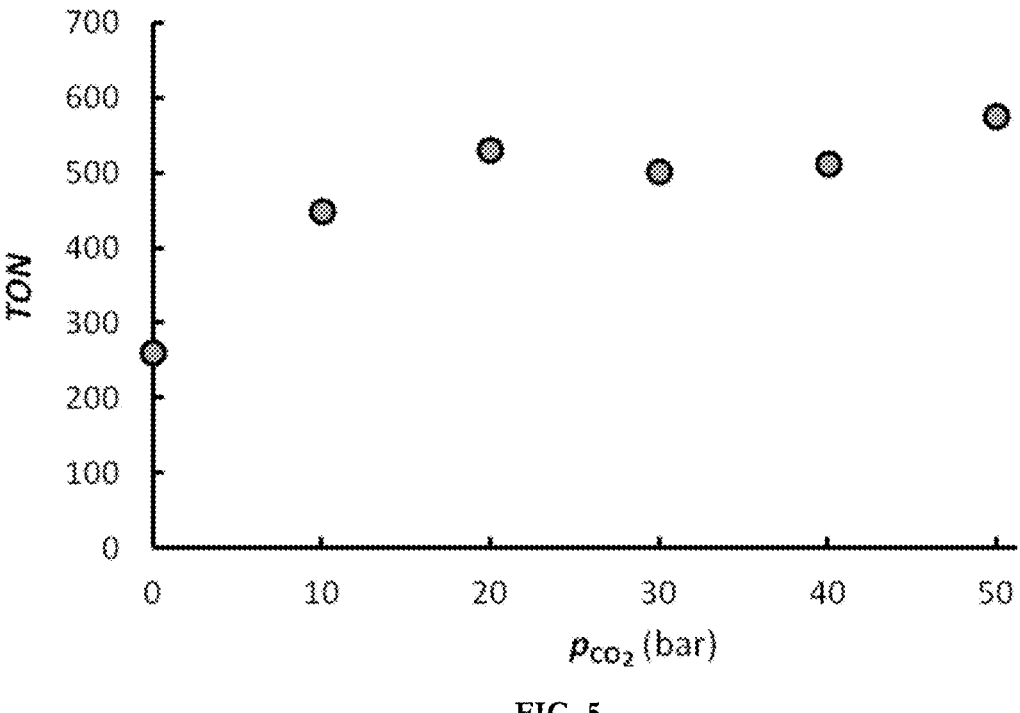
FIG. 5: The change of the catalytic cycle number (TON) values as a function of the applied $CO_2$ pressure–using [Ir(emim)(cod)(mtppms]+mtppts catalyst in a batch reactor with a total volume of 600 ml.
Figure 6:
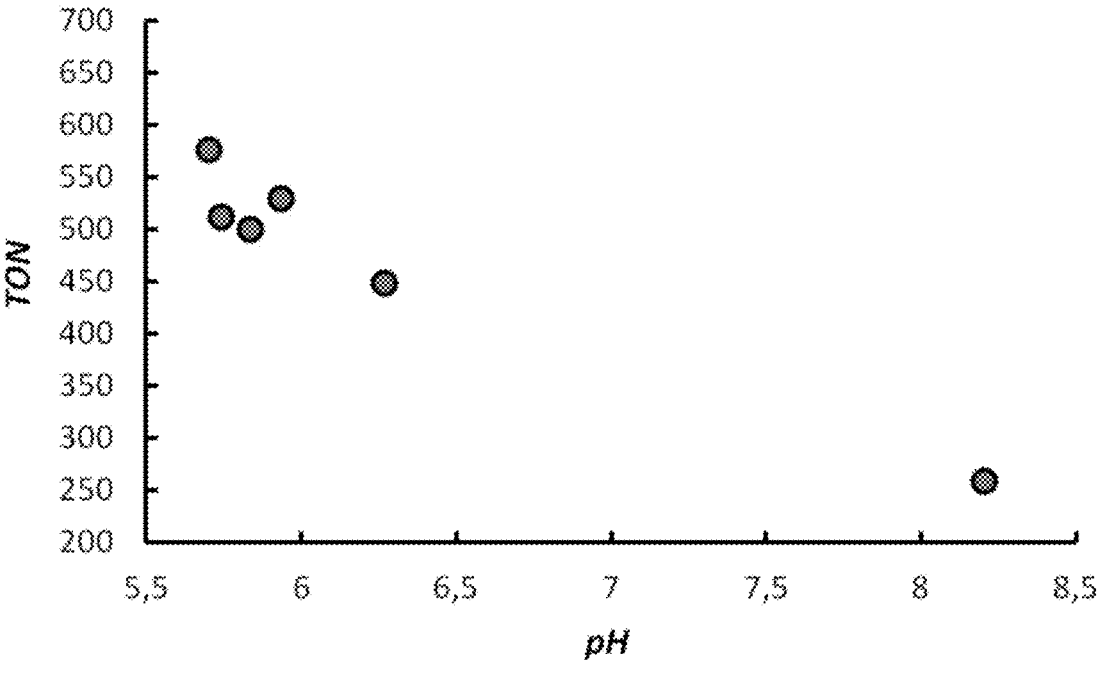
FIG. 6: The change of the catalytic cycle number (TON) values as a function of pH using [Ir(emim)(cod)(mtppms]+mtppts catalyst in a batch reactor with a total volume of 600 ml.

From the data in FIG. 5, we determined the change in the catalytic cycle number as a function of pH by using the data in FIG. 2 mentioned in Example 1 (change in pH with increasing $CO_2$ pressure). The obtained results are shown in FIG. 6.

Example 4: Investigation of the Effect of $CO_2$ on the Activity of the Catalyst [Ir(Bmim)(Cod)(Mtppms]+Mtppts The general formula of the tested catalyst is [[Ir(bmim)(cod)(mtppms]+mtppts, where bmim is 1-butyl-3-methyl-imidazol-2-ylidene, cod is 1,5-cyclooctadiene, mtppms is monosulfonated triphenylphosphine and mtppts is trisulfonated triphenylphosphine.

Reaction mixture: in a 100.0 and 600.0 ml constant temperature batch reactor (100 and 600 ml Series 5500 HP Compact Reactor manufactured by Parr Instruments):

20.0 and 200.0 ml solution volume,
80° C.,
$[Ir]=0.0005$ mol/dm$^3$ and $0,00005$ mol/dm$^3$,
$[mtppms]=[Ir]$,
$[mtppts]=0,001$ mol/dm$^3$ and $0,0001$ mol/dm$^3$,
$[HCO_3Na]=0.1$ mol/dm$^3$
$p(H_2)=50$ bar,
$p(CO_2)=0$ or 50 bar
reaction time=1 hour.

TABLE 1

| | The obtained catalytic cycle number (TON) values | |
|---|---|---|
| TON | 50 bar $H_2$ | 50 bar $H_2$ + 50 bar $CO_2$ |
| 100 ml reactor | 144 | 212 |
| 600 ml reactor | 368 | 808 |

In summary, we found that by changing the pressure of $CO_2$ from 0 to 50 bar (under the reaction conditions used), the achieved TON value increases from 144 to 212 and from 368 to 808, which also in this case is due to the effect of $CO_2$ means a significant increase in reaction rate.

Example 5: Investigation of the Effect of $CO_2$ on the Activity of the [Ir(Hexmim)(Cod)(Mtppms]+Mtppts Catalyst The general formula of the investigated catalyst is [Ir(hexmim)(cod)(mtppms]+mtppts, where hexmim is 1-hexyl-3-methylimidazol-2-ylidene, cod is 1,5-cyclooctadiene, mtppms is monosulfonated triphenylphosphine and mtppts is trisulfonated triphenylphosphine.

Reaction mixture: in a 100.0 and 600.0 ml constant temperature batch reactor (100 and 600 ml Series 5500 HP Compact Reactor manufactured by Parr Instruments):

20.0 and 200.0 ml solution volume,
80° C.,
$[Ir]=0.0005$ mol/dm$^3$ and $0,00005$ mol/dm$^3$,
$[mtppms]=[Ir]$,
$[mtppts]=0,001$ mol/dm$^3$ and $0,0001$ mol/dm$^3$,
$[HCO_3Na]=0.1$ mol/dm$^3$
$p(H_2)=50$ bar,
$p(CO_2)=0$ or 50 bar
reaction time=1 hour.

TABLE 2

| | The obtained catalytic cycle number (TON) values | |
|---|---|---|
| TON | 50 bar $H_2$ | 50 bar $H_2$ + 50 bar $CO_2$ |
| 100 ml reactor | 134 | 204 |
| 600 ml reactor | 285 | 522 |

In summary, we found that by changing the $CO_2$ pressure from 0 to 50 bar (under the reaction conditions used), the achieved TON value increases from 134 to 204 and from 285 to 522, which in this case is also due to the effect of $CO_2$ means a significant increase in reaction rate.

Example 6: Investigation of the Effect of $CO_2$ on the Activity of the Catalyst [Ir(2Mim)(Cod)(Mtppms]+Mtppts The general formula of the tested catalyst is [Ir(2mim)(cod)(mtppms]+mtppts, where 2mim is 1,3-dimethylimidazol-2-ylidene, cod is 1,5-cyclooctadiene, mtppms is monosulfonated triphenylphosphine and mtppts is trisulfonated triphenylphosphine.

Reaction mixture: in a 100.0 and 600.0 ml constant temperature batch reactor (100 and 600 ml Series 5500 HP Compact Reactor manufactured by Parr Instruments):

20.0 and 200.0 ml solution volume,

80° C.,

[Ir]=0.0005 mol/dm³ and 0,00005 mol/dm³,

[mtppms]=[Ir],

[mtppts]=0,001 mol/dm³ and 0,0001 mol/dm³,

[HCO₃Na]=0.1 mol/dm³ p(H₂)=50 bar, p(CO₂)=0 or 50 bar reaction time=1 hour.

TABLE 3

| The obtained catalytic cycle number (TON) values | | |
|---|---|---|
| TON | 50 bar H₂ | 50 bar H₂ + 50 bar CO₂ |
| 100 ml reactor | 158 | 256 |
| 600 ml reactor | 228 | 786 |

In summary, we found that by changing the $CO_2$ pressure from 0 to 50 bar (under the reaction conditions used), the achieved TON value increases from 158 to 256 and from 228 to 786, which is also in this case the effect of $CO_2$ means a significant increase in reaction rate.

Example 7: Investigation of the Effect of $CO_2$ on the Activity of the Catalyst [Ir(Bnmim)(Cod)(Mtppms]+Mtppts The general formula of the tested catalyst is [Ir(Bnmim)(cod)(mtppms]+mtppts, where Bnmim is 1-benzyl-3-methylimidazol-2-ylidene, cod is 1,5-cyclooctadiene, mtppms is monosulfonated triphenylphosphine and mtppts is trisulfonated triphenylphosphine.

Reaction mixture: in a 100.0 and 600.0 ml constant temperature batch reactor (100 and 600 ml Series 5500 HP Compact Reactor manufactured by Parr Instruments):

20.0 and 200.0 ml solution volume,

80° C.,

[Ir]=0.0005 mol/dm³ and 0,00005 mol/dm³,

[mtppms]=[Ir],

[mtppts]=0,001 mol/dm³ and 0,0001 mol/dm³,

[HCO₃Na]=0.1 mol/dm³ p(H₂)=50 bar, p(CO₂)=0 or 50 bar reaction time=1 hour.

TABLE 4

| The obtained catalytic cycle number (TON) values | | |
|---|---|---|
| TON | 50 bar H₂ | 50 bar H₂ + 50 bar CO₂ |
| 100 ml reactor | 121 | 262 |
| 600 ml reactor | 361 | 1119 |

In summary, we found that by changing the $CO_2$ pressure from 0 to 50 bar (under the reaction conditions used), the achieved TON value increases from 121 to 262 and from 361 to 1119, which is also in this case the effect of $CO_2$ means a significant increase in reaction rate.

Example 8: Investigation of the Effect of $CO_2$ on the Activity of the [Ir(Emim)(Cod)(Mtppms]+Pta Catalyst The general formula of the tested catalyst is [Ir(emim)(cod)(mtppms]+pta, where emim is 1-ethyl-3-methylimidazol-2-ylidene, cod is 1,5-cyclooctadiene, mtppms is monosulfonated triphenylphosphine and pta is 1,3,5-triaza-7-phosphadamantane.

Reaction mixture: in a 100.0 and 600.0 ml constant temperature batch reactor (100 and 600 ml Series 5500 HP Compact Reactor manufactured by Parr Instruments):

20.0 and 200.0 ml solution volume,

80° C.,

[Ir]=0.0005 mol/dm³ and 0,00005 mol/dm³,

[mtppms]=[Ir],

[pta]=0,001 mol/dm³ and 0,0001 mol/dm³,

[HCO₃Na]=0.1 mol/dm³ p(H₂)=50 bar, p(CO₂)=0 or 50 bar reaction time=1 hour.

TABLE 5

| The obtained catalytic cycle number (TON) values | | |
|---|---|---|
| TON | 50 bar H₂ | 50 bar H₂ + 50 bar CO₂ |
| 100 ml reactor | 67 | 108 |
| 600 ml reactor | 260 | 1084 |

In summary, we found that by changing the $CO_2$ pressure from 0 to 50 bar (under the reaction conditions used), the achieved TON value increases from 67 to 108 and from 260 to 1084, which in this case is also due to the effect of $CO_2$ means a significant increase in reaction rate.

Example 9: Investigation of the Effect of $CO_2$ on the Activity of the [Ir(Emim)(Cod)(Mtppms]+Mtppms Catalyst The general formula of the tested catalyst is [Ir(emim)(cod)(mtppms]+mtppms, where emim is 1-ethyl-3-methylimidazol-2-ylidene, cod is 1,5-cyclooctadiene, mtppms is monosulfonated triphenylphosphine.

Reaction mixture: in a 100.0 and 600.0 ml constant temperature batch reactor (100 and 600 ml Series 5500 HP Compact Reactor manufactured by Parr Instruments):

20.0 and 200.0 ml solution volume,

80° C.,

[Ir]=0.0005 mol/dm³ and 0,00005 mol/dm³,

[mtppms]=0.0015 mol/dm³ and 0,00015 mol/dm³,

[HCO₃Na]=0.1 mol/dm³ p(H₂)=50 bar, p(CO₂)=0 or 50 bar reaction time=1 hour.

19 20

TABLE 6

| The obtained catalytic cycle number (TON) values | | |
| --- | --- | --- |
| TON | 50 bar $H_2$ | 50 bar $H_2$ + 50 bar $CO_2$ |
| 100 ml reactor | 263 | 320 |
| 600 ml reactor | 325 | 2050 |

In summary, we found that by changing the $CO_2$ pressure from 0 to 50 bar (under the applied reaction conditions), the achieved TON value increases from 263 to 320 and from 325 to 2050, which in this case is also due to the effect of $CO_2$ means a significant increase in speed.

Figure 7:
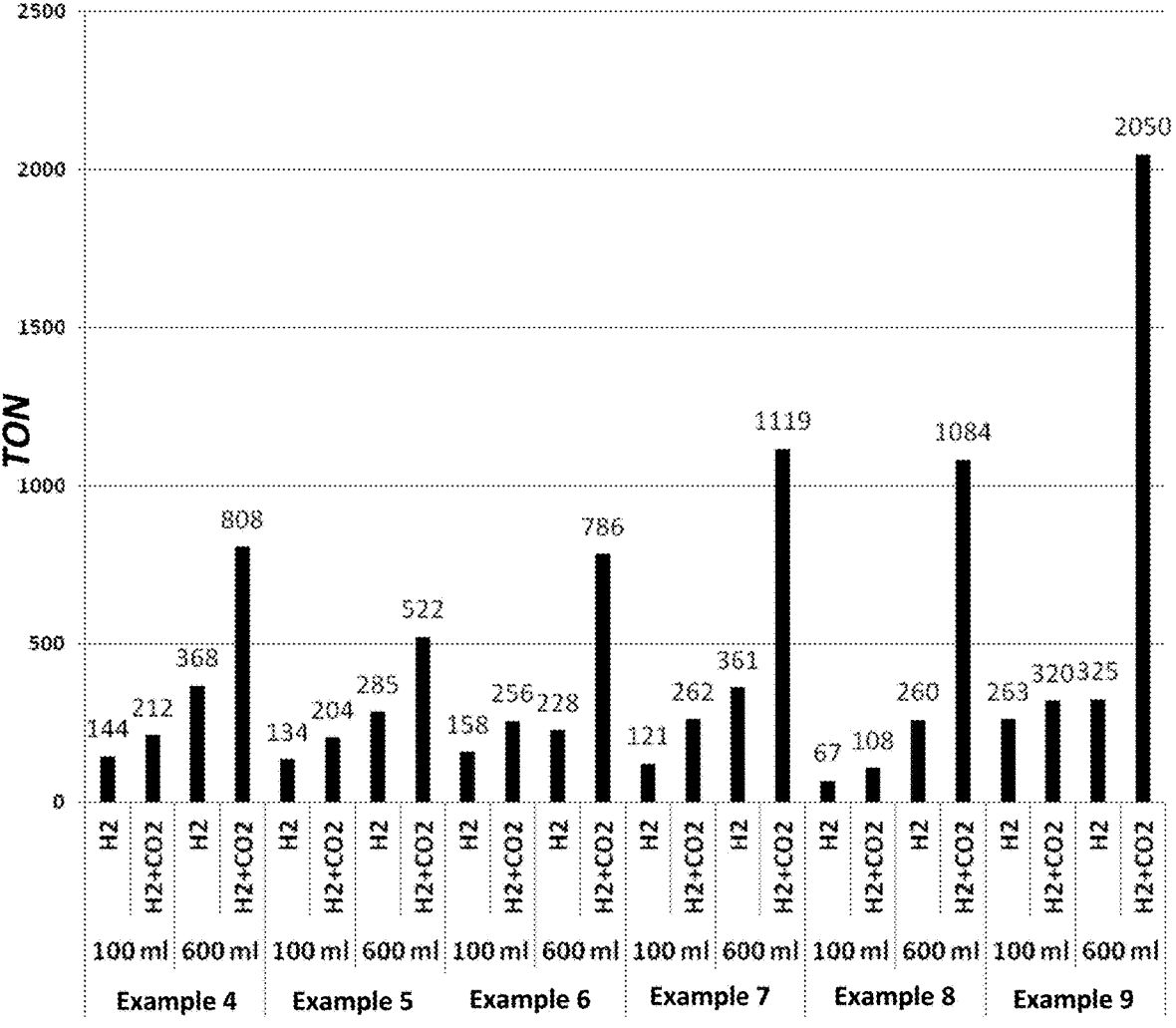
FIG. 7: Comparison of catalytic cycle number (TON) values obtained in Examples 4-7.

FIG. 7 provides a visual presentation of the results presented in Examples 4-9. The results clearly prove that both in the case of changing the carbene ligand and the phosphine ligand, it can be proven that in the presence of $CO_2$ (under the given conditions) the rate of hydrogenation of bicarbonate increases several times (2-6 times).

INDUSTRIAL APPLICABILITY

The process for the hydrogenation of hydrogen carbonate, which is the subject of our invention, provides an opportunity to provide a renewable energy source, the basis of which is a process for the catalytic decomposition of formate in an aqueous reaction system and the production of hydrogen gas free of $CO_x$ by-products, and for the catalytic hydrogenation of hydrogen carbonate produced in the same reaction system in an aqueous reaction system in the presence of carbon dioxide in the gas space, and thus to produce the corresponding formate.

What is claimed is:

1. A process for the hydrogenation of hydrogen carbonate ($HCO_3^-$), in an aqueous reaction system, said hydrogen carbonate being selected from sodium hydrogen carbonate ($NaHCO_3$), lithium hydrogen carbonate ($LiHCO_3$), cesium hydrogen carbonate ($CsHCO_3$) and potassium hydrogen carbonate ($KHCO_3$) and for the production of formate, selected from the group of sodium formate (HCOONa), lithium formate (HCOOLi), cesium formate (HCOOCs) and potassium formate (HCOOK), said process comprising bringing said hydrogen carbonate and a catalyst into contact with each other at an elevated temperature and, at a pressure of 1-1200 bar;

where the catalyst is a catalyst with the general formula $[Ir(cod)(NHC)P_a]+nP_b$, where in the formula Ir is iridium;

cod is 1,5-cyclooctadiene;

NHC is an N-heterocyclic carbene;

n is an integer from 1 to 4; and $P_a$ and $P_b$ are independently 1,3,5-triaza-7-phosphaadamantane (pta), monosulfonated triphenylphosphine (mtppms) or trisulfonated triphenylphosphine (mtppts);

characterized in that the hydrogenation of hydrogen carbonate is carried out in such a way that carbon dioxide is present in the gas space.

2. The process according to claim 1, characterized in that the catalyst used is selected from the following:

a) a catalyst according to the formula [Ir(emim)(cod)(mtppms)]+mtppts, wherein emim is 1-ethyl-3-methyl-imidazol-2-ylidene, cod is 1,5-cyclooctadiene, mtppms is monosulfonated triphenylphosphine and mtppts is trisulfonated triphenylphosphine;

b) a catalyst according to the formula [Ir(bmim)(cod)(mtppms]+mtppts, wherein bmim is 1-butyl-3-methyl-imidazol-2-ylidene, cod is 1,5-cyclooctadiene, mtppms is monosulfonated triphenylphosphine and mtppts is trisulfonated triphenylphosphine;

c) a catalyst according to the formula [Ir(hexmim)(cod)(mtppms]+mtppts, wherein hexmim is 1-hexyl-3-methylimidazol-2-ylidene, cod is 1,5-cyclooctadiene, mtppms is monosulfonated triphenylphosphine and mtppts is trisulfonated triphenylphosphine;

d) a catalyst according to the formula [Ir(2mim)(cod)(mtppms]+mtppts, wherein 2mim is 1,3-dimethyl-imidazol-2-ylidene, cod is 1,5-cyclooctadiene, mtppms is monosulfonated triphenylphosphine and mtppts is trisulfonated triphenylphosphine;

e) a catalyst according to the formula [Ir(Bnmim)(cod)(mtppms]+mtppts, wherein Bnmim is 1-benzyl-3-methylimidazol-2-ylidene, cod is 1,5-cyclooctadiene, mtppms is monosulfonated triphenylphosphine and mtppts is trisulfonated triphenylphosphine;

f) a catalyst according to the formula [Ir(emim)(cod)(mtppms]+pta, wherein emim is 1-ethyl-3-methylimidazol-2-ylidene, cod is 1,5-cyclooctadiene, mtppms is monosulfonated triphenylphosphine and pta is 1,3,5-triaza-7-phosphadamantane; and g) a catalyst according to the formula [Ir(emim)(cod)(mtppms]+mtppms, wherein emim is 1-ethyl-3-methylimidazol-2-ylidene, cod is 1,5-cyclooctadiene, mtppms is monosulfonated triphenylphosphine.

3. The process according to claim 1, wherein the temperature is in the range of 60° C. to 100° C.

4. The process according to claim 1, wherein the temperature is 80° C.

5. The process according to claim 1, wherein the pressure is in the range of 10 bar to 100 bar.

6. The process according to claim 1, wherein the N-heterocyclic carbene is 1-R-3-methylimidazol-2-ylidene, where R is C1-C6 alkyl or benzyl.

7. A process for decomposing a formate selected from sodium formate (HCOONa), lithium formate (HCOOLi), cesium formate (HCOOCs) and potassium formate (HCOOK) in an aqueous reaction system and for producing hydrogen gas ($H_2$) free of $CO_x$ by-products, and in the same reaction system, for the hydrogenation of the resulting hydrogen carbonate ($HCO_3^-$) selected from the group of sodium hydrogen carbonate ($NaHCO_3$), lithium hydrogen carbonate ($LiHCO_3$), cesium hydrogen carbonate ($CsHCO_3$) and potassium hydrogen carbonate ($KHCO_3$) in an aqueous reaction system, thus for the production of a formate selected from the group of sodium formate (HCOONa), lithium formate (HCOOLi), cesium formate (HCOOCs) and potassium formate (HCOOK);

where the reactants and the reaction products are formed in a reversible reaction cycle by using the reaction system of the formate decomposition step and the bicarbonate hydrogenation step and by choosing the values of temperature, pressure and pH within the ranges specified below, and this reaction cycle is repeated the required number of times;

where the formate decomposition step includes bringing the formate into contact with the catalyst in an aqueous reaction system, at an elevated temperature and, at a pH greater than 8, in an Ar gas atmosphere;

where the hydrogenation step of the hydrogen carbonate includes bringing the hydrogen carbonate and a catalyst into contact with each other, at an elevated temperature, under pressure of 1-1200 bar;

where the catalyst is a catalyst with the general formula
[Ir(cod)(NHC)P$_a$]+nP$_b$,
where in the formula
Ir is iridium;
cod is 1,5-cyclooctadiene;
NHC is an N-heterocyclic carbene;
n is an integer from 1 to 4; and
P$_a$ and P$_b$ are independently a 1,3,5-triaza-7-phosphada-
mantane (pta), monosulfonated triphenylphosphine
(mtppms) or trisulfonated triphenylphosphine (mtppts);
characterized in that the hydrogenation of hydrogen car-
bonate is carried out in such a way that carbon dioxide
is present in the gas space.

8. The process according to claim 7, characterized in that
the catalyst used is selected from the following:

a) a catalyst according to the general formula [Ir(emim)
(cod)(mtppms]+mtppts, where emim is 1-ethyl-3-
methylimidazol-2-ylidene, cod is 1,5-cyclooctadiene,
mtppms is monosulfonated triphenylphosphine and
mtppts is trisulfonated triphenylphosphine;

b) a catalyst according to the general formula [Ir(bmim)
(cod)(mtppms]+mtppts, where bmim is 1-butyl-3-
methylimidazol-2-ylidene, cod is 1,5-cyclooctadiene,
mtppms is monosulfonated triphenylphosphine and
mtppts is trisulfonated triphenylphosphine;

c) a catalyst according to the general formula [Ir(hexmim)
(cod)(mtppms]+mtppts, where hexmim is 1-hexyl-3-
methylimidazol-2-ylidene, cod is 1,5-cyclooctadiene,
mtppms is monosulfonated triphenylphosphine and
mtppts is trisulfonated triphenylphosphine;

d) a catalyst according to the general formula [Ir(2mim)
(cod)(mtppms]+mtppts, where 2mim is 1,3-dimethyl-
imidazol-2-ylidene, cod is 1,5-cyclooctadiene, mtppms
is monosulfonated triphenylphosphine and mtppts is
trisulfonated triphenylphosphine;

e) a catalyst according to the general formula [Ir(Bnmim)
(cod)(mtppms]+mtppts, where Bnmim is 1-benzyl-3-
methylimidazol-2-ylidene, cod is 1,5-cyclooctadiene, mtppms is monosulfonated triphenylphosphine and
mtppts is trisulfonated triphenylphosphine;

f) a catalyst according to the general formula [Ir(emim)
(cod)(mtppms]+pta, where emim is 1-ethyl-3-methyl-
imidazol-2-ylidene, cod is 1,5-cyclooctadiene, mtppms
is monosulfonated triphenylphosphine and pta is 1,3,
5-triaza-7-phosphadamantane; and g) a catalyst according to the general formula [Ir(emim)
(cod)(mtppms]+mtppms, where emim is 1-ethyl-3-
methylimidazol-2-ylidene, cod is 1,5-cyclooctadiene,
mtppms is monosulfonated triphenylphosphine.

9. A method for storing hydrogen comprising the process
of claim 7.

10. A method for storing hydrogen comprising the process
of claim 9 wherein said storing is for a hydrogen battery.

11. The method of storing hydrogen of claim 9 wherein
said storing is for hydrogen required to operate a fuel cell or
other equipment requiring H$_2$ and further optionally com-
prising releasing of said hydrogen to an extent necessary to
operate said fuel cell or other equipment.

12. The process according to claim 7, wherein the tem-
perature is in the range of 60° C. to 100° C. during the
formate decomposition step.

13. The process according to claim 7, wherein the tem-
perature is 80° C. during the formate decomposition step.

14. The process according to claim 7, wherein the
pH=8.3±0.2 during the formate decomposition step.

15. The process according to claim 7, wherein the tem-
perature is in the range of 60° C. to 100° C. during the
hydrogenation step.

16. The process according to claim 7, wherein the tem-
perature is 80° C. during the hydrogenation step.

17. The process according to claim 7, wherein the pres-
sure is in the range of 10 bar to 100 bar during the
hydrogenation step.

18. The process according to claim 7, wherein the N-het-
erocyclic carbene is 1-R-3-methylimidazol-2-ylidene, where
R is C1-C6 alkyl or benzyl.

* * * * *